United States Patent [19]
Libin

[11] Patent Number: 5,945,089
[45] Date of Patent: Aug. 31, 1999

[54] METHOD OF TREATING MUCOSITIS

[75] Inventor: Barry Libin, Bellport, N.Y.

[73] Assignee: I-Dent International Corporation, Bellport, N.Y.

[21] Appl. No.: 09/186,825

[22] Filed: Nov. 5, 1998

[51] Int. Cl.$^6$ ........................... A61K 7/22; A61K 31/075
[52] U.S. Cl. ............................................. 424/54; 514/721
[58] Field of Search ................................ 424/54; 514/721

[56] References Cited

U.S. PATENT DOCUMENTS

| | | | |
|---|---|---|---|
| 4,961,926 | 10/1990 | Gabrilove | 424/85.1 |
| 5,188,820 | 2/1993 | Cummins et al. | |
| 5,236,699 | 8/1993 | Libin | 424/54 |
| 5,286,492 | 2/1994 | Dettmar et al. | |
| 5,496,828 | 3/1996 | Cullinan | 514/324 |
| 5,855,872 | 1/1999 | Libin | |

FOREIGN PATENT DOCUMENTS

| | | |
|---|---|---|
| 0455475 | 11/1991 | European Pat. Off. |
| 0528468 | 2/1993 | European Pat. Off. |
| 2207604 | 2/1989 | United Kingdom |
| 9325209 | 12/1993 | WIPO |

OTHER PUBLICATIONS

Computer Print Out, Dated 1998.
Letter from Sharon F. Suer of Oct. 22, 1998, Computer Print Out Dialog Re: Apr. 1993 Publication of IMS Word Files.
Letter from Andy Ingram of IMS World, Dated Oct. 22, 1998.
Letter from IMS Health to Linda Raffensberger with attached page of New Product Launch, Letter dated Mar. 30, 1992.
Min. Stom., 28, 1979, pp. 209–213.
J. Dental Research, 68, pp. 1706–1707 (1989).
Int. J. of Cos. Science, vol. 13, No. 1, Feb. 1991, p. 1706.
J. Clin. Oncology, vol. 12, No. 12, 1994, pp. 2630,2637.
Decision of Board of Patent Appeals and Interferences, Serial No. 08/051,861 (1998).
Examiner's Answer, Serial No. 08/051,861 (1995).

*Primary Examiner*—Raymond Henley, III
*Attorney, Agent, or Firm*—Hedman, Gibson & Costigan, P.C.

[57] ABSTRACT

A method of treating mucositis in immunocompromised patients is disclosed which is based on contacting the affected area with an amount of composition which comprises triclosan in an amount which is effective to alleviate the symptoms of mucositis.

5 Claims, No Drawings

METHOD OF TREATING MUCOSITIS

BACKGROUND OF THE INVENTION

Immunodeficient patients frequently exhibit a condition on the oral mucosa which is clinically described as oral mucositis. This condition has no known microbial or viral vector that has been implicated as the causative agent. The immunodeficiency that preceded the appearance of mucositis may arise spontaneously from genetic factors, may be caused by infections, e.g., the HIV virus or mucositis be induced as a result of chemotherapy or radiation therapy for neoplastic diseases. This condition has been difficult to treat and has not responded to treatment with antimicrobial agents.

The applicant has discovered a treatment for mucositis which is based on contacting the diseased sites on the affected area of the mucosa with triclosan. The present inventor holds U.S. Pat. No. 5,236,699, which is incorporated by reference. That patent describes the use of a mouth rinse which contains triclosan and a cationic antibacterial agent for use inter alia the treatment of plaque and gum diseases.

SUMMARY OF THE INVENTION

The present invention comprises a method of treating mucositis which comprises applying to the affected area an effective amount of a composition which comprises triclosan.

It is a primary object of the invention to provide a method for treating oral mucositis in immunocompromised patients.

It is also an object of the invention to provide a method for treating mucositis using of triclosan.

These and other objects of the invention will become apparent from a review of the appended specification.

DETAILED DESCRIPTION OF THE PRESENT INVENTION

Mucositis is treated in accordance with the present invention by contacting the involved oral mucosa of an immunocompromised patient who is afflicted with mucositis with a composition which contains an amount of triclosan which is effective to treat mucositis. Generally these compositions contain in combination, about 0.01 to 5.3 wt % and preferably 0.1 to 0.5 wt % of triclosan. Generally, semi-solid formulations will be formulated with higher levels of triclosan. The amount of the combined formulation which is applied will depend on the extent of the lesion. Generally when a liquid formulation is applied to a typical lesion, from 5 ml to 30 ml is applied to the lesion as a mouth rinse with the patient being instructed to eject the excess amount of the formulation from the mouth without swallowing. If a semi-solid formulation is used, then a thin film, i.e. from 0.5 mm to 5 mm in thickness may be applied to the affected area.

Triclosan is 2,4,4'-trichloro-2'-hydroxydiphenyl ether which is commercially available.

The triclosan is adsorbed and retained on the oral mucosa while resisting removal by saliva in the oral cavity.

The compositions may be prepared as a liquid or a semi-solid formulation. The semi-solid compositions may vary from highly viscous liquids to gels or paste like formulations.

A liquid formulation may be prepared with purified water, the triclosan and a solubilizer. The solubilizer may comprise a poloxamer. These materials are of the formula $HO(CH_2CH_2O)_a (CH(CH_3) (CH_2OH)_b(CH_2CH_2O)_cH$ where b is at least 15 and $(CH_2CH_2O)_a+c$ is varied from 20 to 90% by weight and the weight average mol wt ranges from 10,000 to >16,000. The polyoxamers are available under the Pluronic trademark and Pluronic F127 is a preferred solubilizer. If solubilizer is employed, it will comprise from 0.5 to 8 wt % of the liquid composition. Generally, only liquid compositions in water will require a solubilizer; semi-solid formulations will not require the presence of a solubilizer.

The mucositis treating formulation may include an anticaries agent which is soluble in water such as sodium fluoride, stannous fluoride or sodium monofluorophosphate in an amount which is effective to inhibit tooth decay in an immunocompromised patient. Generally, this amount will be from 0.01 to 4% by weight, based on the weight of the fluoride ion. The amount may be varied depending on the particular source of the fluoride ion which is chosen. Certified color may be added in a minor amount e.g. 0.1 % by weight. FD&C Blue No.1 or FD&C Yellow No.5 may be used as desired.

A typical liquid formulation will comprise:

|  | % weight |
|---|---|
| triclosan | 0.100 |
| Sorbitol Solution, U.S.P. | 12.000 |
| Glycerin | 10.000 |
| Sodium Saccharin, U.S.P | 0.100 |
| Pluronic F127, NF | 4.000 |
| 190 Proof Grain Alcohol, U.S.P. | 7.000 |
| Peppermint 1FL2745 | 0.152 |
| Caramel Color AP100 | 0.0085 |
| Purified water | 66.639 |

A typical fluoridated liquid formulation will comprise:

|  | % weight |
|---|---|
| triclosan | 0.100 |
| Sodium Fluoride | 0.020 |
| Sorbitol Solution, U.S.P. | 11.980 |
| Glycerin | 10.000 |
| Sodium Saccharin, U.S.P | 0.100 |
| Pluronic F127, NF | 4.000 |
| 190 Proof Grain Alcohol, U.S.P. | 7.000 |
| Peppermint 1FL2745 | 0.152 |
| Caramel Color AP100 | 0.0085 |
| Purified water | 66.639 |

A typical semisolid formulation which is a cream: will include:

| triclosan | 0.1–5.3 wt % |
|---|---|
| Cetaryl glucoside and cetaryl alcohol (Emulgade PL 68/50, Henkel) | 0.5–6.7 wt % |
| Cetaryl alcohol (Lanette, Henkel) | 0.5–7.7 wt % |
| Coco-Caprylate (Cedol LC, Henkel) | 0.5–6.0 wt % |
| Dicapryl ether (Cetiet, Henkel) | 0.25–5.0 wt % |
| Sweet almond oil | 0.25–5.0 wt % |
| Petrolatum | 0.5–6.0 wt % |
| Dimethicone (Silicone DC 200CS/Dow) | 0.1–5 wt % |
| Phase B | |
| glycerin | 0.5–4.6 wt % |
| Sodium methylparaben/Sodium paraben or | 0.01–0.03 wt % |
| Sodium benzoate | 0.25–0.3 wt % |
| Deionized water | 10–90 wt % |

An example of a semi-solid formulation according to the invention is as follows:

| Phase A | |
|---|---|
| triclosan | 0.3 wt % |
| Cetaryl glucoside and cetaryl alcohol (Emulgade PL 68/50, Henkel) | 3.7 wt % |
| Cetaryl alcohol (Lanette, Henkel) | 3.7 wt % |
| Coco-Caprylate (Cedol LC, Henkel) | 3.0 wt % |
| Dicapryl ether (Cetiet, Henkel) | 2.0 wt % |
| Sweet almond oil | 2.0 wt % |
| Petrolatum | 3.0 wt % |
| Dimethicone (Silicone DC 200CS/Dow) | 0.6 wt % |
| Phase B | |
| Glycerin | 2.6 wt % |
| Sodium methylparaben | 0.18 wt % |
| Sodium paraben | 0.02 wt % |
| Deionized water to | 100.0 wt % |
| Phase C | |
| Tocopheryl acetate (cophenol 1260/Henkel) | 1.0 wt % |

The composition is prepared by separately heating Phase A and Phase B to 80° C. prior to forming these phases. Phase C is added with stirring at 55° C. until a smooth homogeneous mixture is obtained.

The foregoing description of a preferred embodiment of the invention has been presented for purposes of illustration and description. It is not intended to be exhaustive or to limit the invention to the precise form disclosed. Obvious modifications or variations are possible in light of the above teachings. All such obvious modifications and variations are intended to be within the scope of the appended claims.

I claim:

1. A method of treating mucositis in an immunocompromised patient, said method comprising contacting the affected diseased sites with an amount of composition which comprises triclosan which is effective to alleviate the symptoms of mucositis.

2. A method of treating mucositis as defined in claim 1 wherein the triclosan is combined in a liquid formulation with a solubilizer.

3. A method of treating mucositis as defined in claim 1 wherein the triclosan is in a semi-solid formulation.

4. A method of treating mucositis in an immunocompromised patient, said method comprising contacting the affected area with an amount of composition which consists essentially of triclosan in an amount which is effective to alleviate the symptoms of mucositis.

5. A method of treating mucositis in an immunocompromised patient as defined in claim 1 wherein the composition includes a fluoride.

* * * * *